United States Patent [19]

Jacquet et al.

[11] 4,150,115
[45] Apr. 17, 1979

[54] QUATERNIZED POLYAMINE POLYMERS AND COSMETIC COMPOSITIONS CONTAINING THE SAME

[75] Inventors: Bernard Jacquet, Antony; Gérard Lang, Epinay-sur-Seine, both of France

[73] Assignee: L'Oreal, Paris, France

[21] Appl. No.: 742,118

[22] Filed: Nov. 15, 1976

[30] Foreign Application Priority Data

Nov. 13, 1975 [LU] Luxembourg .......................... 73795

[51] Int. Cl.² .................... A61K 7/06; A61K 7/09; A61K 7/11; A61K 31/74
[52] U.S. Cl. ........................................... 424/70; 8/10.2; 8/11; 260/567.6 P; 424/45; 424/71; 424/72; 424/78; 424/80; 424/DIG. 1; 424/DIG. 2; 424/DIG. 3; 424/DIG. 4
[58] Field of Search .................. 260/567.6 P; 424/72, 424/70, 71, 78, DIG. 1, DIG. 2, DIG. 3, DIG. 4; 8/10.2

[56] References Cited

U.S. PATENT DOCUMENTS 3,235,596  2/1966  Nordgren et al. ............ 260/567.6 P
3,778,476  12/1973  Rembaum et al. ............ 260/567.6 P

FOREIGN PATENT DOCUMENTS 1492021  6/1969  Fed. Rep. of Germany ............. 8/10.2

Primary Examiner—Frederick E. Waddell
Attorney, Agent, or Firm—Cushman, Darby & Cushman

[57] ABSTRACT

Quaternized polyamine polymers are employed in cosmetic compositions for application to the hair or skin. The polymer has recurring units of the formula:

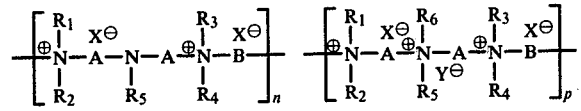

wherein A is polymethylene having 2–10 carbon atoms, B is selected from polymethylene having 3–10 carbon atoms, xylylidenyl group —CH$_2$—C$_6$H$_4$—CH$_2$— ortho, meta or para, —(CH$_2$)$_x$—O—(CH$_2$)$_x$— wherein x is 2 or 3, or —CH$_2$—CHOH—CH$_2$—; R$_1$ and R$_3$ represent an aliphatic radical having 1–12 carbon atoms; R$_2$ and R$_4$ represent an aliphatic radical having 1–20 carbon atoms; R$_5$ is hydrogen or an aliphatic, alicyclic, aryl or arylaliphatic radical containing 1–20 carbon atoms; R$_6$ is an aliphatic or arylaliphatic radical containing 1–20 carbon atoms; X is a halide anion; Y is selected from a halide anion, SO$_4$H$^\ominus$ or CH$_3$SO$_4^\ominus$; and n and p are whole numbers with p being able to be 0, such that the ratio p/n+p ranges from 0 to 0.95.

19 Claims, No Drawings

QUATERNIZED POLYAMINE POLYMERS AND COSMETIC COMPOSITIONS CONTAINING THE SAME

The present invention relates to the use of aminated polymers having quaternized ammonium groups as a cosmetic agent.

Certain polymers having quaternized nitrogen atoms in their macrochain are known and have been proposed for use as pesticidal agents, as flocculating agents, as surface-active agents or as ion exchange resins.

It has now surprisingly been discovered that certain aminated polymers having quaternized ammonium groups exhibit interesting cosmetic properties when they are utilized in cosmetic compositions to be applied to living human hair or human skin.

Thus, the present invention relates to the use, as a cosmetic agent, and principally the use in the production of cosmetic compositions, of polymers having recurring units of the following formula:

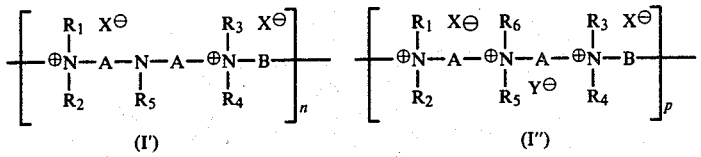

wherein
  A is polymethylene having 2 to 10 carbon atoms;
  B is selected from polymethylene having from 3 to 10 carbon atoms; a xylylidenyl group, $-CH_2-C_6H_4-CH_2-$, ortho, meta or para; a $-(CH_2)_x-O-(CH_2)_x-$group, x being 2 or 3; or a $-CH_2-CHOH-CH_2-$group;
  $R_1$ and $R_3$ each independently represent an aliphatic radical having from 1-12 carbon atoms;
  $R_2$ and $R_4$ each independently represent an aliphatic radical having from 1-20 carbon atoms;
  $R_5$ is hydrogen or an aliphatic, alicyclic, aryl or arylaliphatic radical containing a maximum of 20 carbon atoms;
  $R_6$ is an aliphatic or arylaliphatic radical containing a maximum of 20 carbon atoms;
  $X^\ominus$ represents a halide anion, principally, chloride or bromide;
  $Y^\ominus$ is a halide anion, principally chloride or bromide, or bisulfate anion, $SO_4H^\ominus$ or methosulfate anion, $CH_3SO_4^\ominus$;
  n and p are whole numbers with the number p being able to be equal to 0, such that the ratio $p/n+p$ can vary from 0 to 0.95.

In that which follows, polymers consisting only of units I' are called polymers of formula I'. Polymers consisting of both units I' and I'' are called polymers of formula I''. To designate indifferently the polymers I' and I'', the term employed is polymers of formula I.

In the polymers of formula I:
  $R_1$ and $R_3$ represent, principally, alkyl having from 1-12 carbon atoms;
  $R_2$ and $R_4$ represent, principally, alkyl having 1-20 carbon atoms;
  when $R_5$ or $R_6$ represents an aliphatic radical, this radical is generally alkyl or cycloalkyl wherein the alkyl has at most 20 carbon atoms, and preferably from 1-16 carbon atoms; when $R_5$ represents an alicyclic radical, this radical is generally cycloalkyl having 5 or 6 chains; when $R_5$ or $R_6$ represents an arylaliphatic radical, this radical is generally aralkyl such as phenylalkyl wherein the alkyl moiety has preferably from 1-3 carbon atoms and is, particularly, benzyl.

Preferably $R_1=R_3=CH_3$ with $R_2=R_4$.

The terminal groups of the polymers of formula I' can be $-A-NR_1R_2$, $-A-NR_3R_4$ or $-B-X$.

The terminal groups of the polymers of formula I'' can be $-B-X$ or $-NR_1R_2R_6^\oplus Y^\ominus$ or $-NR_3R_4R_6^\oplus Y^\ominus$.

The polymers of formula I' can be prepared by condensing a triamine of formula II:

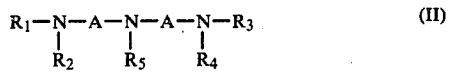

with an essentially equimolar amount of a dihalide of formula III:

wherein $R_1$, $R_2$, $R_3$, $R_4$, $R_5$, A, B and X are defined above.

The polymers of formula I'' can be prepared by polycondensing compounds of formulas II and III as set out above and then reacting the resulting intermediate polymer of formula I' with a compound of formula $R_6$-Y, $R_6$ and Y being defined as above.

The compound $R_6$-Y can be reacted either by adding the same to the reaction mixture, or by first isolating the intermediate polymer I' and redissolving it in an appropriate solvent and then adding thereto the said $R_6$-Y compound.

In the two processes described above, the polycondensation reaction can be carried out in a solvent or in a mixture of solvents favoring quaternization reactions. Representative solvents include water, dimethyl formamide, acetonitrile and lower alcohols, principally lower alkanols such as methanol and the like.

The temperature of the reaction can vary between 10 and 150° C., and preferably between 20 and 100° C.

The time of the reaction depends on the nature of the solvent selected, the initial reactants chosen and the degree of polymerization desired.

The resulting polycondensate is isolated if desired at the termination of the reaction by, for instance, either filtration or by concentrating the reaction mixture.

The average length of the polymer chain can be regulated by adding at the beginning of the reaction or in the course thereof a small quantity, 1-15 mole percent, relative to one of the reactants II or III of a mon-functional reactant such as a tertiary amine.

In this case, a portion at least of the terminal groups of the resulting polymer I comprises the tertiary amine group utilized. The present invention also relates to the cosmetic use of the polymers of formula I having such terminal groups.

In the two above described procedures for preparing polymers of formula I, the final product is isolated at the termination of the reaction either by filtration or by concentration of the reaction mixture. Optionally, the isolated polymer can be subjected to a crystallization technique by the addition of an appropriate anhydrous organic liquid.

The polymers of formula I″ are prepared by using reactant $R_6$-Y in any amount up to a maximum of 3 moles per mole of starting triamine. Preferably, from 0.1 to 3 moles of $R_6$-Y per mole of triamine are employed. The polymers of formula I″ are then isolated under conditions favoring the removal of excess $R_6$-Y reactant.

In accordance with the procedures outlined above, an extensive variety of polymers I″ can be obtained. They can include those having very few units of formula I″ (p/n+p close to 0) up to those which include very few units of formula I′ (p/n+p being then equal or slightly lower than 0.95).

The polymers I″ include then a statistical distribution of units of formulas I′ and I″.

The initial triamines used in the present invention can be obtained in accordance with methods described in the literature.

For example, the pentamethylated $N_1,N_1,N_2,N_3,N_3$-dialkylenetriamines can be prepared by methylating corresponding dialkylenetriamines with formaldehyde and formic acid.

The same method can be employed to produce triamines of the formula:

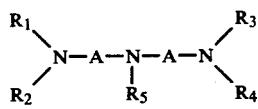

wherein: A= $(CH_2)_2$; and $R_1=R_2=R_3=R_4=CH_3$, with $R_5$ being different from H and from $CH_3$.

Initial triamines wherein $R_1=R_2=R_3=R_4=H$ can be prepared in accordance with British Pat. No. 913,471. This same method can also be employed to produce triamines of the above formula wherein: $R_1=R_3=CH_3$ and $R_2=R_4=R_5\neq CH_3$, starting with triamines wherein: $R_1=R_3=H$, which in turn can be prepared in accordance with a technique analogous to that described by F. B. Zienty, J.A.C.S., 68 p. 1388, 1945.

Triamines where: $R_1=R_2=R_3=R_4=R_5\neq CH_3$, can be prepared by a method described in U.S. Pat. No. 3,324,182.

Finally, triamines wherein: $R_1=R_3$, $R_2=R_4$ and $R_5\neq CH_3$; can be prepared according to S. M. Kupchan, G. Bondesson and A. P. Davies, J. of Medicinal Chemistry, 15 (1), p. 65, 1972.

Although the invention is not limited to the use of polymers I having any particular degree of polymerization, generally the polymers of formula I according to the present invention have a molecular weight ranging between 5,000 and 100,000.

The polymers are generally soluble in at least one of three solvents comprising water, ethanol or a water-ethanol mixture.

On evaporation of their solution, it is possible to obtain films which exhibit good affinity with the hair.

As indicated above, the polymers of formula I exhibit interesting cosmetic properties which permit their use in the preparation of cosmetic compositions.

The present invention thus also relates to cosmetic compositions will include at least one polymer of formula I. These cosmetic compositions also contain at least one conventional cosmetic carrier or vehicle. The cosmetic compositions of the present invention include the polymer of formula I either as the principal active component or as an additive.

These cosmetic compositions can be provided principally in the form of an aqueous, alcoholic or hydroalcoholic solution, the alcohol being principally a lower alkanol such as ethanol or isopropanol, or in the form of a cream, a gel, an emulsion or even in the form of an aerosol packaged under pressure in an aerosol container together with a propellant.

Adjuvants are generally present in the cosmetic compositions of the present invention. Representative adjuvants include perfumes, dyes, preservatives, sequesterants, thickening agents and the like.

The cosmetic compositions of the present invention are of the ready-to-use type or they can be concentrates which are to be diluted before use. Thus the cosmetic compositions of the present invention need not be limited to any particular concentration of the polymer of formula I, suffice it to say that when employed, an effective amount of polymer I is present to accomplish the intended purpose of its use.

Generally, however, in the cosmetic compositions of the invention, the concentration of the polymers of formula I ranges between 0.01 and 10 weight percent, principally between 0.5 and 10 weight percent and preferably between 0.5 and 5 weight percent.

The polymers of formula I exhibit interesting cosmetic properties when they are applied to the hair. Thus when they are applied to the hair, either alone or with other active substances, during such hair treating operations as a shampoo, a hair dye treatment, a hair setting operation and the like, they significantly improve the qualities of the hair. For example, they facilitate the untangling of moist hair and even when present in high concentrations they do not impart to wet hair a sticky feeling.

Contrary to conventional cationic agents, the polymers of this invention do not render dry hair dull or heavy, thus facilitating the attainment of bouffant coiffures. They also impart to dry hair the qualities of liveliness and a shiny appearance. Further, the polymers of this invention effectively contribute to the elimination of defects of hair sensitized by such treatments as bleachings, permanent waving or hair dyeing operations. In effect, it is known that sensitized hair is often dry, dull and rough, difficult to untangle and to style.

The polymers of the present invention exhibit, particularly great interest when they are employed as pre-treating agents, especially before an anionic and/or non-ionic shampooing or before an oxidation dyeing which in turn is followed by an anionic and/or non-ionic shampooing. When so employed, the hair is particularly easy to untangle and has a very soft touch or feel.

The polymers of this invention are also useful as pre-treating agents in other hair treating operations such as a permanent wave treatment.

Thus, the cosmetic compositions of the present invention can be cosmetic compositions for the hair comprising at least one polymer of formula I and at least one adjuvant conventionally employed in cosmetic compositions for the hair.

These cosmetic compositions for the hair can be provided in the form of an aqueous, alcoholic or hydroalcoholic solution, the alcohol being preferably a lower alkanol such as ethanol or isopropanol, or in the form of a cream, a gel, or an emulsion or even in the form of a spray. They can also be packaged in the form of an aerosol, together with a propellant such as for example nitrogen, nitrous oxide or chlorofluorinated hydrocarbons of the Freon type.

Representative adjuvants generally present in the cosmetic compositions for the hair include perfumes, dyes, preservatives, sequesterants, thickening agents, emulsifiers and the like or even resins conventionally employed in cosmetic compositions for the hair.

The polymers of formula I can be present in these cosmetic compositions for the hair, either as an additive or as the principal active component. Representative compositions wherein the polymer can function as a principal active component include hair setting lotions, hair treating lotions, hair styling creams or gels. Representative compositions where the polymer can function as an additive include shampoo compositions, hair setting compositions, permanent waving compositions, hair dye compositions, hair restructuring lotions, anti-seborrheic treating lotions or hair lacquer compositions.

The cosmetic compositions for the hair according to the invention thus include principally:

(a) hair treating lotion compositions comprising as the active component at least one polymer of formula I in an aqueous or hydroalcoholic solution. The amount of the polymer of formula I present in these compositions can vary between 0.01 and 10 percent by weight and preferably between 0.1 and 5 percent by weight. The pH of these lotions is close to neutral and can vary for example from 6 to 8. If necessary the pH can be adjusted to the value desired, by adding either an acid, such as citric acid or a base, such as an alkanolamine, for instance, monoethanolamine or triethanolamine.

To treat the hair with such a lotion, the same is applied to wet hair and is permitted to remain in contact therewith for 3–15 minutes. Thereafter the hair is rinsed and, if desired, set;

(b) shampoo compositions comprising at least one polymer of formula I and a cationic, non-ionic or anionic detergent. Representative cationic detergents include long chain quaternary ammoniums, esters of fatty acids and amino alcohols, or polyether amines. Representative non-ionic detergents which can be used in admixture with the anionic detergents include: (1) alcohols, diols, alkyl phenols, thiols or amides having $C_{12}$–$C_{18}$ linear chains which can be oxyethylenated, oxypropylated, glycerolated or glycidoled; (2) $C_2$ to $C_{12}$ alcohols, thiols or alkyl phenols which are oxyethylenated and/or oxypropylated; (3) polycondensates of ethylene oxide and propylene oxide; and (4) compounds of the formula:

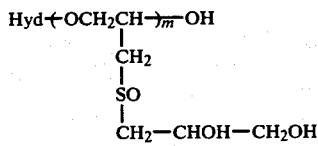

where m is a whole number and Hyd represents a hydrocarbon radical.

Representative anionic detergents include the alkaline salts, magnesium salts, ammonium salts, amine salts or amino alcohol salts (principally ethanolamine or isopropanolamine) of fatty acids such as oleic acid, ricinoleic acid, fatty acids of copra or hydrogenated copra oil; alkylsulfates wherein the alkyl moiety is linear and has 12 to 18 carbon atoms; sulfated and ethoxylated $C_{12}$ to $C_{18}$ linear alkylamides, $C_{12}$ to $C_{18}$ linear α-olefin sulfonates; carboxylic acids of polyglycolic ethers having the formula Alk—(OCH$_2$—CH$_2$—)$_m$—OCH$_2$CO$_2$H wherein Alk is a $C_{12}$ to $C_{18}$ linear chain and m is a whole number; the condensation products of fatty acids with: sarcosine and its derivatives, isethionates, polypeptides, alkylsulfosuccinates or their derivatives, taurine, methyl taurine and the like; the sulfosuccinates of $C_{12}$—$C_{18}$ ethoxylated alcohols or their corresponding $C_{12}$—$C_{18}$ amide derivatives; and the alkylbenzenesulfonates, alkylarylpolyether sulfates, monoglyceride sulfates and the like.

All these anionic detergents, as well as numerous others not cited here, are well known and are described in the literature.

These compositions in the form of shampoos can also contain various adjuvants such as perfumes, dyes, preservatives, thickening agents, foam stabilizing agents, softening agents, or even one or more cosmetic resins.

In these shampoo compositions, the concentration of the detergent generally ranges between 5 and 30 weight percent and the concentration of the polymer of formula I ranges between 0.01 and 3 weight percent, preferably between 0.3 and 2 weight percent.

(c) hair setting lotions, principally for sensitized hair, comprising at least one polymer of formula I, in an aqueous, alcoholic or hydroalcoholic solution. These hair setting lotions can also contain another cosmetic resin which can be, for instance, vinylic or crotonic homopolymers or copolymers including, for instance, polyvinylpyrrolidone, copolymers of polyvinylpyrrolidone and vinyl acetate, copolymers of crotonic acid and vinyl acetate, and the like.

The concentration of the polymers of formula I present in these hair setting lotions ranges generally between 0.1 and 5 weight percent and preferably between 0.2 and 3 weight percent. The concentration of the other cosmetic resin can vary essentially in the same manner.

The pH of these hair setting lotions ranges generally between 3 and 9 and preferably between 4.5 and 7.5. The pH can be adjusted, if desired, by the addition, for instance, of an alkanolamine such as monoethanolamine or triethanolamine;

(d) hair dye compositions comprising at least one polymer of formula I, a hair dye and a carrier. Preferably, the carrier is selected so as to constitute a cream.

The concentration of the polymer of formula I in these hair dye compositions can range between 0.1 and 10 weight percent, principally between 0.5 and 10 weight percent and preferably between 0.5 and 6 weight percent. However, in these hair dye compositions, the principal active component is the dye (direct dye) or its precursors, and not the polymer of formula I.

It is known that in an oxidation dyeing operation dyes termed oxidation dyes which are aromatic compounds of the diamine, aminophenol or phenol type are employed. These aromatic compounds are transformed into dye compounds by condensation in the presence of an oxidizing agent, generally $H_2O_2$. The ortho- or para-diamines or ortho or para-, mono- or di-aminophenols give on oxidation strongly colored compounds. The meta-diamines, meta-aminophenols and polyphenols give only weak shades. For this reason, the para derivatives are called "bases" and the meta derivatives, and the poly phenols, are called modifiers.

The "bases" principally employed are: p-phenylene diamine, p-toluylenediamine, chloroparaphenylenediamine, p-aminodiphenylamine, o-phenylenediamine, ortho-toluylenediamine, 2,5-diaminoanisole, o-aminophenol and p-aminophenol.

The modifiers principally employed are: m-phenylenediamine, m-toluylenediamine, 2,4-diaminoanisol, m-aminophenol, pyrocatechol, resorcinol, hydroquinone, α-naphthol and 1,5-dihydroxynaphthalene.

The oxidation dyeing compositions contain principally a mixture of bases and modifiers, with a carrier so as to provide the same in the form of a cream or gellable liquid. This composition can also contain a direct hair dye. Further, these oxidation dyeing compositions can be packaged in two parts, one part containing an oxidizing agent such as $H_2O_2$ and the other part containing the remaining components. The two parts are mixed at the time of use. Examples of such compositions and their use are given below;

(e) hair lacquer compositions comprising an alcoholic or hydroalcoholic solution of a conventional hair lacquer cosmetic resin, and at least one polymer of formula I. This solution can be packaged under pressure in an aerosol container and admixed with a propellant.

In accordance with the present invention, an aerosol hair lacquer composition can be prepared by adding a conventional cosmetic resin and the polymer of formula I to a mixture of an anhydrous aliphatic alcohol such as ethanol or isopropanol, and a propellant or a mixture of liquified propellants such as halogenated hydrocarbons of the trichlorofluoromethane or dichlorodifluoromethane type.

In these hair lacquer compositions, the concentration of the conventional cosmetic resin can range generally between 0.5 and 3 weight percent, and the concentration of the polymer of formula I ranges generally between 0.1 and 3 weight percent thereof.

However, it is possible to add to the hair lacquer compositions of the present invention, adjuvants such as dyes, plasticizers or any other conventional adjuvant;

(f) hair restructuring lotions comprising at least one hair restructuring agent and at least one polymer of formula I. Representative hair restructuring agents usefully employed in such lotions include the methylolated derivatives described in French Pat. Nos. 1,519,979; 1,519,980; 1,519,981; 1,519,982; and 1,527,085.

In these lotions, the concentration of the restructuring agent ranges also between 0.1 and 10 weight percent, and the concentration of the polymer of formula I ranges generally between 0.1 and 5 weight percent; and (g) hair pretreatment compositions which can be provided in the form of an aqueous or hydroalcoholic solution, optionally, in an aerosol container, or in the form of a cream or gel. These pretreatment compositions are applied to the hair before a shampooing and principally before an anionic and/or non-ionic shampoo; or before an oxidation dyeing followed by an anionic and/or non-ionic shampoo; or even before a permanent waving treatment.

In these pretreatment compositions, polymer I constitutes the active component, properly speaking, and its concentration therein ranges generally from 0.1 to 10 percent; and in particular from 0.2 to 5 weight percent thereof. The pH of these compositions, preferably close to neutral, can range however, between 3 and 9 and especially between 6 and 8.

These pretreatment compositions can contain various adjuvants, for example, resins, conventionally employed in cosmetic compositions for the hair, pH modifiers, for example, amino alcohols such as monoethanolamine and the like, as indicated for the hair treating lotion compositions described in paragraph (a) above.

The polymers of formula I also exhibit interesting cosmetic characteristics when they are applied to the skin. Principally they favor the hydration of the skin and avoid its drying out. They also impart to the skin a significant softness to the touch.

Thus, cosmetic compositions according to the invention can also be cosmetic compositions for the skin which include at least one polymer of formula I. Moreover, these compositions for the skin can include at least one conventionally employed adjuvant and can be provided in the form of a cream, a gel, an emulsion or an aqueous, alcoholic or hydroalcoholic solution. The concentration of the polymer of formula I in these compositions for the skin ranges generally between 0.1 and 10 weight percent.

Representative adjuvants generally present in these cosmetic compositions include perfumes, dyes, preservatives, thickening agents, sequesterants, emulsifiers and the like.

Representative compositions for the skin include principally treating creams or lotions for the hands or face, anti-solar creams, dye creams, make-up remover milks, foamable liquids for the bath, or even deodorant compositions and can be prepared according to conventional methods.

For example, a cream can be prepared by emulsifying an aqueous phase containing in solution the polymer of formula I and optionally other components or adjuvants, with an oily phase.

The oily phase can comprise various materials, such as paraffin oil, petrolatum oil, sweet almond oil, avocado oil, olive oil, esters of fatty acids such as glyceryl mono-stearate, ethyl or isopropyl palmitates and alkyl myristates such as propyl, butyl or cetyl myristates. Further, fatty alcohols such as cetyl alcohol or waxes such as, for example, beeswax can also be employed.

The polymers of formula I can be present in these cosmetic compositions for the skin either as an additive or as the principal active component in the treating creams or lotions for the hands or face, or as an additive in anti-solar cream compositions, dye creams, make-up remover milks, foaming oils or liquids for the bath and the like.

The present invention relates particularly to cosmetic compositions such as defined above including at least any one of the polymers of formula I described in the following examples. These particular cosmetic compositions are either compositions for the hair, or compositions for the skin.

The present invention also relates to a cosmetic treatment process comprising applying to the hair or to the skin a cosmetic composition containing at least one polymer of formula I defined above.

In particular, the present invention relates to a process for treating hair comprising applying to the hair, before an anionic and/or non-ionic shampoo, or before an oxidation dyeing followed by an anionic and/or non-ionic shampoo, at least one polymer of formula I. The shampoo itself can contain the polymers of formula I or other cationic polymers.

The invention also relates to new polymers comprising recurring units of the formulas

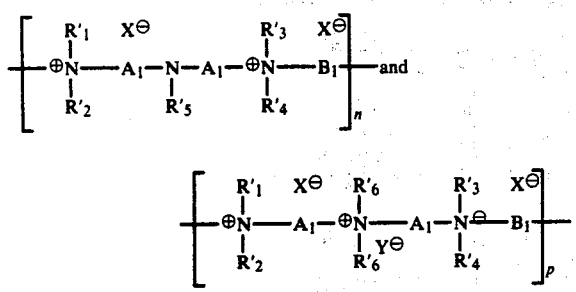

wherein n and p are whole numbers with the number p also being able to be 0, such that the ratio, p/n+p ranges from 0 to 0.95;

$R'_1$ and $R'_3$ each independently represent an aliphatic radical having 1-12 carbon atoms;

$R'_2$ and $R'_4$ each independently represent an aliphatic radical having 1-20 carbon atoms;

$R'_5$ is hydrogen or an aliphatic, alicyclic, aryl or arylaliphatic radical containing a maximum of 20 carbon atoms;

$R'_6$ is an aliphatic or arylaliphatic radical containing a maximum of 20 carbon atoms;

$X^\ominus$ represents a halide anion, principally chloride or bromide;

$Y^\ominus$ represents a halide anion, principally chloride or bromide or a bisulfate anion $SO_4H^\ominus$ or methosulfate $CH_3SO_4^\ominus$;

when one of the radicals $R'_1$ to $R'_5$ is other than $CH_3$, $A_1$ is polymethylene having 2-10 carbon atoms and $B_1$ is selected from polymethylene having 4-10 carbon atoms, a xylylidenyl group —$CH_2$—$C_6H_4$—$CH_2$ (ortho, meta or para), or a —$CH_2$—$CHOH$—$CH_2$ group; and when $R'_1=R'_2=R'_3=R'_4=R'_5=CH_3$, $A_1$ is polymethylene having 4-10 carbon atoms and $B_1$ is selected from polymethylene having 3-10 carbon atoms, a xylylidenyl group —$CH_2$—$C_6H_4$—$CH_2$— (ortho, meta or para) or a —$CH_2$—$CHOH$—$CH_2$ group.

The invention relates principally to polymers comprising recurring units of the formula

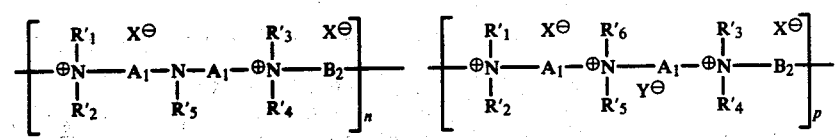

wherein $B_2$ is selected from polymethylene having 4-10 carbon atoms, a xylylidenyl group —$CH_2$—$C_6H_4$—$CH_2$— (ortho, meta or para), or a —$CH_2$—$CHOH$—$CH_2$— group;

$R'_1$ and $R'_3$ each independently represent an aliphatic radical having 1-12 carbon atoms;

$R'_2$ and $R'_4$ each independently represent an aliphatic radical having 1-20 carbon atoms;

$R'_5$ is hydrogen or an aliphatic, alicyclic, aryl or arylaliphatic radical containing a maximum of 20 carbon atoms;

$R'_6$ is an aliphatic or aryl aliphatic radical containing a maximum of 20 carbon atoms;

$X^\ominus$ represents a halide anion, principally chloride or bromide;

$Y^\ominus$ is a halide anion, principally chloride or bromide, or a bisulfate anion $SO_4H^\ominus$ or methosulfate $CH_3SO_4^\ominus$;

when one of the radicals $R'_1$ to $R'_5$ is other than $CH_3$, $A_1$ is polymethylene having 2-10 carbon atoms;

when $R'_1=R'_2=R'_3=R'_4=R'_5=CH_3$, $A_1$ is polymethylene having 4-10 carbon atoms, and n and p are whole numbers with p being able to be 0, such that the ratio p/n+p ranges from 0 to 0.95.

The invention also relates to a process for preparing these new products. This process is analogous to that described above for the preparation of the polymers of formula I.

The present invention also relates to cosmetic compositions such as defined above, containing these new products.

The following non-limiting examples illustrate the present invention. Unless otherwise stated, all parts and percentages are by weight.

Examples of Preparation

EXAMPLE 1

Polymer of formula I' wherein
$R_1=R_2=R_3=R_4=R_5=CH_3$, $A=(CH_2)_2$, $B=(CH_2)_4$,
p=0 and X=Br.

There is heated to reflux for 100 hours a mixture of 17.33 g (0.1 mole) of pentamethyl diethylene triamine and 21.6 g (0.1 mole) of dibromobutane in 150 cc of methanol. The reaction mixture is then concentrated under reduced pressure and the resulting polymer is washed with ethyl ether and dried under reduced pressure. The resulting polymer which contains 38.6% $Br^\ominus$, is soluble in water and slightly soluble in ethanol.

EXAMPLE 2

Polymer of formula I'' wherein
$R_1=R_2=R_3=R_4=R_4=CH_3$, $A=(CH_2)_6$, $B=(CH_2)_4$,
$X=Br$, $R_6=C_4H_9$ and $Y=Br$.

There is heated to reflux for 100 hours a mixture of 48.5 g (0.17 mole) of pentamethyl dihexamethylene triamine and 36.7 g (0.17 mole) of dibromobutane in 320 cc of methanol. There are then slowly added to the reaction mixture 33 g (0.153 mole) of bromobutane and the heating of the resulting reaction mixture is continued for 20 hours. The reaction mixture is then concentrated under reduced pressure and the resulting residue is washed with ethyl ether. The polymer thus obtained which is then filtered and dried under reduced pressure is soluble in a water-ethanol mixture.

By operating in a manner essentially the same as that described in Example 1, the following polymers of formula I' have been prepared.

| Example No. | $R_1$ | $R_2$ | $R_3$ | $R_4$ | A | $R_5$ | B | X | Soluble in |
|---|---|---|---|---|---|---|---|---|---|
| 3 | $CH_3$ | $CH_3$ | $CH_3$ | $CH_3$ | $(CH_2)_{10}$ | $CH_3$ | $(CH_2)_4$ | Br | water-ethanol |

-continued

| Example No. | $R_1$ | $R_2$ | $R_3$ | $R_4$ | A | $R_5$ | B | X | Soluble in |
|---|---|---|---|---|---|---|---|---|---|
| 4 | $CH_3$ | $CH_3$ | $CH_3$ | $CH_3$ | $(CH_2)_{10}$ | $CH_3$ | $(CH_2)_6$ | Br | water-ethanol |
| 5 | $CH_3$ | $CH_3$ | $CH_3$ | $CH_3$ | $(CH_2)_6$ | $CH_3$ | $(CH_2)_4$ | Br | water |
| 6 | $CH_3$ | $CH_3$ | $CH_3$ | $CH_3$ | $(CH_2)_6$ | $CH_3$ | $(CH_2)_6$ | Br | water |
| 7 | $CH_3$ | $CH_3$ | $CH_3$ | $CH_3$ | $(CH_2)_3$ | $CH_3$ | $(CH_2)_4$ | Br | water |
| 8 | $CH_3$ | $C_4H_9$ | $CH_3$ | $C_4H_9$ | $(CH_2)_3$ | $C_4H_9$ | $(CH_2)_4$ | Br | water-ethanol |
| 9 | $C_6H_{13}$ | $C_6H_{13}$ | $C_6H_{13}$ | $C_6H_{13}$ | $(CH_2)_2$ | $C_6H_{13}$ | $(CH_2)_2$-O-$(CH_2)_2$ | Cl | water-ethanol |
| 10 | $CH_3$ | $CH_3$ | $CH_3$ | $CH_3$ | $(CH_2)_2$ | $CH_3$ | p-xylylidenyl | Br | water |
| 11 | $CH_3$ | $CH_3$ | $CH_3$ | $CH_3$ | $(CH_2)_3$ | $CH_3$ | m-xylylidenyl | Br | water |
| 12 | $CH_3$ | $CH_3$ | $CH_3$ | $CH_3$ | $(CH_2)_2$ | $C_{16}H_{33}$ | $(CH_2)_2$-O-$(CH_2)_2$ | Cl | water-ethanol |
| 13 | $CH_3$ | $CH_3$ | $CH_3$ | $CH_3$ | $(CH_2)_2$ | $C_6H_5$ | $CH_2$-CHOH-$CH_2$ | Cl | water |
| 14 | $CH_3$ | $C_6H_{13}$ | $CH_3$ | $C_6H_{13}$ | $(CH_2)_3$ | $C_6H_{13}$ | $(CH_2)_4$ | Br | water-ethanol |

By operating in a manner essentially the same as that described in Example 2, the following polymers of formula I" have been prepared.

EXAMPLE 15

Polymer of formula I" wherein
$R_1=R_2=R_3=R_4=R_6=CH_3$, $R_5$=benzyl, $A=(CH_2)_2$, $B=(CH_2)_6$, $X^\ominus=Br$ and $Y^\ominus=CH_3SO_4^-$ For the quaternization reaction, 0.5 mole of dimethyl sulfide ($R_6Y$ Compound) is employed per mole of the initial triamine reactant. The polymer obtained is soluble in water.

EXAMPLE 16

Polymer of formula I" wherein
$R_1=R_2=R_3=R_4=R_5=CH_3$, $R_6=C_4H_9$, $A=(CH_2)_{10}$ $B=(CH_2)_{10}$ and $X=Y=Br$ For the quaternization reaction, 0.8 mole of bromobutane ($R_6Y$ compound) is employed per mole of the initial triamine reactant. The polymer obtained is soluble in a water-ethanol mixture.

Examples of Cosmetic Compositions

Example I — Treating Cream for the Hands

| 1. A hand treating cream is prepared by admixing: | | |
|---|---|---|
| Petrolatum oil | 10 | g |
| Cetyl alcohol | 6 | g |
| Glyceryl monostearate, self-emulsifiable | 4 | g |
| Triethanolamine | 2 | g |
| Methyl parahydroxy benzoate | 0.1 | g |
| Polymer of Example 1 | 4 | g |
| Water, q.s.p. | 100 | g |

This cream is rubbed into the hands to assure good penetration. The hands thus treated are soft and pleasant to the touch.

2. Essentially similar results are achieved by replacing the 4 grams of the polymer of Example 1 in the above composition by 3.5 g of the polymer of Example 15.

Example II — Hair Dye Cream for an Oxidation Dyeing Operation

| 1. A hair dye cream is prepared by admixing: | |
|---|---|
| Cetyl stearyl alcohol | 20 g |
| Oleic diethanolamide | 4 g |
| Sodium cetyl stearyl sulfate | 3 g |
| Polymer of Example 4 | 5 g |
| Ammonia - 22° Be (11N) | 10 ml |
| Meta diamino anisol sulfate | 0.048 g |
| Resorcinol | 0.420 g |
| Meta amino phenol base | 0.150 g |
| Nitro paraphenylene diamine | 0.085 g |
| Para toluylene diamine | 0.004 g |
| Tetra sodium salt of ethylene diamine tetraacetic acid- Trilon B | 1 g |
| Sodium bisulfite (d = 1.32) | 1.200 g |
| Water, q.s.p. | 100 g |

30 g of this cream mixture are admixed with 45 g of $H_2O_2$ (20 volumes), yielding a cream having a smooth consistency which is pleasant to apply and which adheres well to the hair. After application of the same to the hair, this cream is permitted to remain in contact therewith for 30 minutes, after which the hair is rinsed and dried. On 100% white hair, a blond coloration is obtained. The hair, wet or dry, is easy to untangle and the hair thus treated is shiny and is pleasant and silky to the touch.

| 2. A hair dye cream is prepared by admixing: | |
|---|---|
| Cetyl stearyl alcohol | 20 g |
| Oleic diethanolamide | 4 g |
| Sodium cetyl stearyl sulfate | 3 g |
| Polymer of Example 7 | 5 g |
| Ammonia - 22° Be (11N) | 12 ml |
| Meta diamino anisol sulfate | 0.048 g |
| Resorcinol | 0.420 g |
| Meta amino phenol base | 0.150 g |
| Nitro paraphenylene diamine | 0.085 g |
| Para toluylene diamine | 0.004 g |
| Trilon B | 1 g |
| Sodium bisulfite (d = 1.32) | 1.200 g |
| Water, q.s.p. | 100 g |

30 g of this cream mixture are admixed with 45 g of $H_2O_2$ (20 volumes), yielding a cream having a smooth consistency which is pleasant to apply and which adheres well to the hair. After application to the hair, this cream is permitted to remain in contact therewith for 30 minutes, after which the hair is rinsed and dried. On 100% white hair, a blond coloration is obtained. The hair, wet or dry, is easy to untangle and the hair thus treated is shiny and is pleasant and silky to the touch.

Example III — Shampoo composition

| A shampoo composition prepared by admixing: | | |
|---|---|---|
| $C_{11}$-$C_{14}$ α-diol condensed with 3-4 moles of glycidol | 17 | g |
| Polymer of Example 1 | 3 | g |
| Lactic acid, q.s. pH = 3.5 | | |
| Water, q.s.p. | 100 | cc |

This clear solution when applied to the head provides a sufficiently soft and abundant foam. The wet hair, after rinsing, untangles easily. After drying the hair the same is lively, light and shiny.

Example IV — Daily antiseborrheic untangling lotion

| A lotion is prepared by admixing: | |
|---|---|
| Carboxy methyl cysteine | 0.3 g |
| Polymer of Example 7 | 0.5 g |
| Cationic polyglucosic derivative, sold under the tradename "781568" by National Starch | 0.3 g |
| Ethyl alcohol | 50° |
| KOH, q.s.p. pH = 7 | |
| Water, q.s.p. | 100 cc |

This lotion when applied daily to oily hair significantly improves the appearance of the hair and makes it easy to comb and to style.

Example V — Hair setting lotion for sensitized hair

| 1. A hair setting lotion is prepared by admixing: | |
|---|---|
| Polymer of Example 5 | 0.8 g |
| Copolymer of polyvinyl-pyrrolidone/vinyl acetate, 60/40 | 1.0 g |
| Triethanolamine, q.s. pH = 6 | |
| Water, q.s.p. | 100 ml |

After applying the above lotion to bleached hair, the hair is set and dried. The hair thus treated is hardened and shiny; is silky to the touch and combs easily.

| 2. A hair setting lotion is prepared by admixing: | |
|---|---|
| Polymer of Example 3 | 1 g |
| Copolymer of polyvinyl-pyrrolidone/vinyl acetate, 60/40 | 1 g |
| Triethanolamine, q.s. pH = 7 | |
| Water, q.s.p. | 100 ml |

The above lotion is applied to bleached hair which is then set and dried. Results essentially the same as those achieved in Example V-1 are obtained.

| 3. A hair setting lotion is prepared by admixing: | |
|---|---|
| Polymer of Example 13 | 1.5 g |
| Copolymer of vinyl acetate/crotonic acid, 90/10 | 1.5 g |
| Triethanolamine, q.s. pH = 7.5 | |
| Water, q.s.p. | 100 ml |

The above lotion is applied to bleached hair which is then set and dried. Results essentially equivalent to those achieved in Example V-1 are obtained.

| 4. A hair setting lotion is prepared by admixing: | |
|---|---|
| Polymer of Example 6 | 1.5 g |
| Copolymer of vinyl acetate/crotonic acid, 90/10 | 1.5 g |
| Monoethanolamine, q.s. pH = 7 | |
| Water, q.s.p. | 100 ml |

The above lotion is applied to bleached hair which is then set and dried. Results essentially the same as those achieved in Example V-1 are obtained.

Example VI — Hair treating lotions (application with rinsing)

| 1. 30 ml of the following hair treating lotion are applied to wet, clean hair: | |
|---|---|
| Polymer of Example 5 | 5 g |
| Monoethanolamine, q.s. pH = 7.5 | |
| Water, q.s.p. | 100 ml |

This lotion is permitted to remain in contact with the hair for 5 minutes, after which the hair is rinsed. The wet hair is soft to the touch and easily untangles. The hair is then set and dried and the dry hair combs easily and is shiny, lively and has body.

| 2. 25 ml of the following hair treating lotion are applied to wet, clean hair: | |
|---|---|
| Polymer of Example 6 | 4 g |
| Citric acid, q.s. pH = 6 | |
| Water, q.s.p. | 100 ml |

This lotion is permitted to remain in contact with the hair for 5 minutes, after which the hair is rinsed. The wet hair is soft to the touch and untangles easily. The hair is then set and dried and the dry hair combs easily and is shiny, lively and has body.

Example VII — Hair restructuring lotion (application without rinsing)

| 1. Prior to use, 0.3 g of N,N'-di-(hydroxymethyl) ethylenethiourea (hereafter called compound A) is mixed with 25 ml of the following solution: | |
|---|---|
| Polymer of Example 1 | 0.6 g |
| HCl, q.s. pH = 2.7 | |
| Water, q.s.p. | 100 ml |

The above lotion is applied to washed and dried hair which then combs easily and is silky to the touch. The hair is then set and dried and the dry hair is shiny, lively, has body (fullness), is silky to the touch and combs easily.

| 2. Prior to use, 0.4 g of compound A, above, is mixed with 25 ml of the following solution: | |
|---|---|
| Polymer of Example 10 | 0.5 g |
| Phosphoric acid, q.s. pH = 2.7 | |
| Water, q.s.p. | 100 ml |

The above lotion is applied to washed and dried hair which then combs easily and is silky to the touch. The hair is then set and dried and the dry hair is shiny, lively, has volume, is silky to the touch and combs easily.

| 3. Prior to use, 0.5 g of compound A, above, are mixed with 25 ml of the following solution: | |
|---|---|
| Polymer of Example 11 | 0.8 g |
| Phosphoric acid, q.s. pH = 3 | |
| Water, q.s.p. | 100 ml |

The above lotion is applied to washed and dried hair which then combs easily and is silky to the touch. The hair is then set and dried and the dry hair is shiny, lively, has fullness, is silky to the touch and combs easily.

| 4. Prior to use, 0.6 g of compound A is mixed with 25 ml of the following solution: | |
|---|---|
| Polymer of Example 13 | 0.7 g |

|  |  |
|---|---|
| HCl, q.s. pH = 3 | |
| Water, q.s.p. | 100 ml |

The above lotion is applied to washed and dried hair which then combs easily and is silky to the touch. The hair is then set and dried and the dry hair is shiny, lively, has fullness, is silky to the touch and combs easily.

Example VIII — Hair restructuring lotion (application with rinsing)

| 1. Prior to use, 1.9 g of compound A are mixed with 25 ml of the following solution: | |
|---|---|
| Polymer of Example 5 | 4 g |
| HCl, q.s. pH = 2.5 | |
| Water, q.s.p. | 100 ml |

The above lotion is applied to washed and dried hair and is permitted to remain in contact therewith for 10 minutes. Thereafter the hair is rinsed and the wet hair is easy to comb and is soft and silky to the touch. The hair is then set and dried under a hood. The dry hair combs easily and is shiny, lively and has body.

| 2. Prior to use, 2 g of compound A are mixed with 25 ml of the following solution: | |
|---|---|
| Polymer of Example 15 | 6 g |
| Phosphoric acid, q.s. pH = 3 | |
| Water, q.s.p. | 100 ml |

The above lotion is applied to washed and dried hair and is permitted to remain in contact therewith for 10 minutes. Thereafter the hair is rinsed and the wet hair is easy to comb and is silky to the touch. The hair is then set and dried under a hood. The dry hair combs easily and is shiny, lively and has body.

| 3. Prior to use, 1.6 g of compound A are mixed with 25 ml of the following solution: | |
|---|---|
| Polymer of Example 6 | 4 g |
| HCl, q.s. pH = 3 | |
| Water, q.s.p. | 100 ml |

The above lotion is applied to washed and dried hair and is permitted to remain in contact therewith for 10 minutes. Thereafter, the hair is rinsed and the wet hair is easy to comb and is silky to the touch. The hair is then set and dried under a hood. The dry hair combs easily and is shiny, lively and has body.

Example IX — Shampoo-dye compositions

| 1. A shampoo-dye composition is prepared by admixing: | |
|---|---|
| Nonyl phenol oxyethylenated with 4 moles of ethylene oxide | 24 g |
| Nonyl phenol oxyethylenated with 9 moles of ethylene oxide | 24 g |
| Polymer of Example 2 | 4 g |
| Ethyl alcohol, 96° titer | 8 g |
| Propylene glycol | 14 g |
| Ammonia - 22° (11N) | 10 cc |
| Meta diamino anisole sulfate | 0.040 g |
| Resorcinol | 0.400 g |
| Meta amino phenol base | 0.150 g |
| Para amino phenol base | 0.087 g |
| Nitro paraphenylene diamine | 1.000 g |
| Trilon B | 3.000 g |
| Sodium bisulfite (d = 1.32) | 1.300 g |
| Water, q.s.p. | 100 g |

50 g of this formulation are mixed with an equal amount of $H_2O_2$ (20 volumes). The resulting gel is then applied to the hair with a brush and permitted to remain in contact therewith for 30 minutes. The hair is then rinsed and the wet hair combs easily. The hair is then set and dried and the dry hair is shiny, lively, has body, is silky to the touch and combs easily. On deep brown hair, a chestnut coloration is obtained.

| 2. A shampoo-dye composition is prepared by admixing: | |
|---|---|
| Nonyl phenol oxyethylenated with 4 moles of ethylene oxide | 25 g |
| Nonyl phenol oxyethylenated with 9 moles of ethylene oxide | 23 g |
| Polymer of Example 8 | 5 g |
| Ethyl alcohol, 96° titer | 7 g |
| Propylene glycol | 13 g |
| Ammonia - 22° Be (11N) | 10 cc |
| Meta diamino anisole sulfate | 0.030 g |
| Resorcinol | 0.400 g |
| Meta amino phenol base | 0.150 g |
| Para amino phenol base | 0.087 g |
| Nitro paraphenylene diamine | 1.000 g |
| Trilon B | 3.000 g |
| Sodium bisulfite (d = 1.32) | 1.200 g |
| Water, q.s.p. | 100 g |

50 g of this formulation are mixed with an equal amount of $H_2O_2$ (20 volumes). The resulting gel is then applied to the hair with a brush and permitted to remain in contact therewith for 30 minutes. The hair is then rinsed and the wet hair combs easily and is silky to the touch. The hair is then set and dried and the dry hair is shiny, lively, has body, is silky to the touch and combs easily. On deep brown hair, a chestnut coloration is obtained.

Example X — Pre-shampoo composition

| 1. 10 g of the following pre-shampoo treating composition are applied to dry, dirty hair: | |
|---|---|
| Polymer of Example 13 | 2 g |
| Monoethanolamine, q.s. pH = 7 | |
| Water, q.s.p. | 100 cc |

The above composition is permitted to remain in contact with the soiled hair for two minutes, after which the hair is given a two stage anionic shampoo treatment. The hair is then rinsed and the wet hair is easy to comb and is soft to the touch. The hair is then set and dried and the dry hair is shiny, combs easily and is silky to the touch. This same composition can be packaged as an aerosol.

| 2. 15 g of the following pre-shampoo treating composition are applid to dry, dirty hair: | |
|---|---|
| Polymer of Example 15 | 1.2 g |
| Polymer of Example 11 | 0.8 g |
| Monoethanolamine, q.s. pH = 7 | |
| Water, q.s.p. | 100 cc |

The above composition is permitted to remain in contact with the soiled hair for two minutes, after which the hair is given a two stage anionic shampoo treatment. The hair is then rinsed and the wet hair is easy to comb and is soft to the touch. The hair is then set and dried and the dry hair is easy to comb, is soft to the touch and is shiny and lively. This same composition can be packaged under pressure in an aerosol container together with nitrogen, or nitrous oxide or a Freon material as the propellant.

Example XI — Pre-dye hair treating lotion 20 cc of the following pre-hair dyeing lotion composition are applied to dirty, dry hair:

| | |
|---|---|
| Polymer of Example 1 | 3.5 g |
| Monoethanolamine, q.s. pH = 8 | |
| Water, q.s.p | 100 g |

The above composition is permitted to remain in contact with the hair for 5 minutes, after which the hair is given a conventional ammoniacal oxidation dyeing treatment. During this treatment, the oxidation dye composition is permitted to remain in contact with the hair for 30 minutes. Thereafter, the hair is rinsed and given an anionic shampoo treatment. The hair is then rinsed and the wet hair combs easily. The hair is then set and dried and the dry hair is silky, shiny and is easy to style.

Example XII — Anionic shampoo composition

An anionic shampoo composition is prepared by admixing:

| | |
|---|---|
| Triethanolamine lauryl sulfate | 10 g |
| Polymer of Example 6 | 1.5 g |
| Triethanolamine, q.s. pH = 8 | |
| Water, q.s.p. | 100 g |

Example XIII — Pre-shampoo composition in aerosol form

A pre-shampoo composition in aerosol form is produced by initially preparing the following solution:

| | |
|---|---|
| Polymer of Example 13 | 7 g |
| Monoethanolamine, q.s. pH = 7 | |
| Water, q.s.p. | 100 g |

30 g of this solution are introduced into an aerosol container together with nitrogen until a pressure of 12 kg/cm² is obtained. Hair which is to be washed is then impregnated with the above composition, released from the container, and is permitted to remain in contact therewith for a few minutes. Thereafter the hair is given a conventional anionic shampoo treatment.

Example XIV — Pre-shampoo composition in the form of a foamable aerosol

A pre-shampoo composition in the form of a foamable aerosol is prepared by admixing the following components and packaging the mixture under pressure in an aerosol container:

| | |
|---|---|
| Sodium cetyl stearyl sulfate | 1.3 g |
| Nonyl phenol ethoxylated with 4 moles of ethylene oxide | 2.0 g |
| Nonyl phenol ethoxylated with 9 moles of ethylene oxide | 2.0 g |
| Polymer of Example 1 | 3.0 g |
| Water | 81.5 g |
| Mixture of dichlorotetrafluoroethane and dichlorodifluoromethane, 70:30 | 10.0 g |
| Amount of filling: 65% | |

The above aerosol composition is released onto dirty, dry hair as a foam which is then rubbed into the hair to assure good distribution therethrough. The hair is then given a conventional anionic shampoo treatment, the anionic shampoo composition being permitted to remain in contact with the hair for 2–3 minutes. Thereafter the hair is rinsed and the wet hair is soft to the touch and combs easily. The hair is then set and dried and the dry hair combs easily, is shiny, lively and has body.

What is claimed is:

1. A cosmetic composition comprising at least one polymer having recurring units of the formula

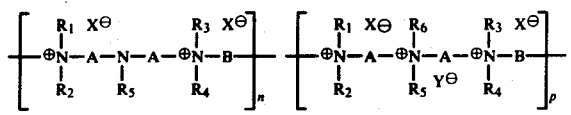

wherein

A is polymethylene having 2–10 carbon atoms;

B is selected from polymethylene having 3–10 carbon atoms, xylylidenyl —CH$_2$—C$_6$H$_4$—CH$_2$— ortho, meta or para, —(CH$_2$)$_x$—O—(CH$_2$)$_x$— wherein x is 2 or 3, or —CH$_2$—CHOH—CH$_2$—;

R$_1$ and R$_3$ each independently represent alkyl having 1–12 carbon atoms;

R$_2$ and R$_4$ each independently represent alkyl having 1–20 carbon atoms;

R$_5$ is hydrogen or alkyl, aryl or arylalkyl containing a maximum of 20 carbon atoms or cycloalkyl having 5 or 6 carbon atoms;

R$_6$ is alkyl or arylalkyl containing a maximum of 20 carbon atoms;

X$^\ominus$ is a halide anion;

Y$^\ominus$ is selected from a halide anion, SO$_4$H$^\ominus$ or CH$_3$SO$_4$$^\ominus$; and n and p are whole numbers with p being able to be 0, such that the ratio p/n+p ranges from 0 to 0.95, said polymer being present in an amount between 0.01 and 10 percent by weight thereof and a cosmetic carrier applicable to the hair or skin.

2. The composition of claim 1 wherein said polymer is present in an amount between 0.5 and 10 weight percent thereof.

3. The composition of claim 2 which is an oxidation hair dye composition.

4. The composition of claim 2 which is a pretreatment composition for application to the hair prior to an anionic or non-ionic shampooing, or before an oxidation dyeing followed by an anionic or non-ionic shampooing, or before a permanent waving treatment.

5. A cosmetic treatment process comprising applying to the hair or skin an effective amount of the cosmetic composition of claim 1.

6. The process of claim 5 which comprises applying said cosmetic composition to the hair prior to an anionic or non-ionic shampoo, or prior to an oxidation dyeing followed by an anionic or non-ionic shampoo.

7. A cosmetic composition for application to the hair comprising at least one polymer having recurring units of the formula

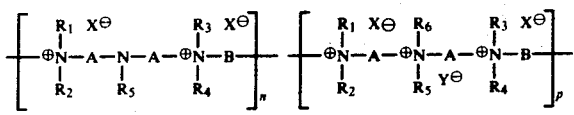

wherein
A is polymethylene having 2-10 carbon atoms;
B is selected from polymethylene having 3-10 carbon atoms, xylylidenyl —CH$_2$—C$_6$H$_4$—CH$_2$— ortho, meta or para, —(CH$_2$)$_x$—O—(CH$_2$)$_x$— wherein x is 2 or 3, or —CH$_2$—CHOH—CH$_2$—;
R$_1$ and R$_3$ each independently represent alkyl having 1-12 carbon atoms;
R$_2$ and R$_4$ each independently represent alkyl having 1-20 carbon atoms;
R$_5$ is hydrogen or alkyl, aryl or arylalkyl containing a maximum of 20 carbon atoms or cycloalkyl having 5 or 6 carbon atoms;
R$_6$ is alkyl or arylalkyl containing a maximum of 20 carbon atoms;
X$^\ominus$ is a halide anion;
Y$^\ominus$ is selected from a halide anion, SO$_4$H$^\ominus$ or CH$_3$SO$_4{}^\ominus$; and
n and p are whole numbers with p being able to be 0, such that the ratio p/n+p ranges from 0 to 0.95, said polymer being present in an amount of 0.01-10 percent by weight thereof and an effective amount of at least one adjuvant employed in cosmetic compositions for the hair, said adjuvant being selected so as to provide one of a hair setting lotion, a hair pre-treating lotion, a hair styling cream or gel, a shampoo composition, a permanent waving composition, a hair dye composition, a hair restructuring lotion, an anti-seborrheic treating lotion or a hair lacquer composition.

8. A cosmetic composition for application to the skin comprising at least one polymer having recurring units of the formula

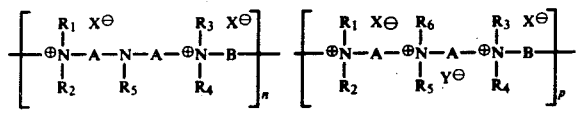

wherein
A is polymethylene having 2-10 carbon atoms;
B is selected from polymethylene having 3-10 carbon atoms, xylylidenyl —CH$_2$—C$_6$H$_4$—CH$_2$— ortho, meta or para, —(CH$_2$)$_x$—O—(CH$_2$)$_x$— wherein x is 2 or 3, or —CH$_2$—CHOH—CH$_2$—;
R$_1$ and R$_3$ each independently represent alkyl having 1-12 carbon atoms;
R$_2$ and R$_4$ each independently represent alkyl having 1-20 carbon atoms;
R$_5$ is hydrogen or alkyl, aryl or arylalkyl containing a maximum of 20 carbon atoms or cycloalkyl having 5 or 6 carbon atoms;
R$_6$ is alkyl or arylalkyl containing a maximum of 20 carbon atoms;
X$^\ominus$ is a halide anion;
Y$^\ominus$ is selected from a halide anion, SO$_4$H$^\ominus$ or CH$_3$SO$_4{}^\ominus$; and
n and p are whole numbers with p being able to be 0, such that the ratio p/n+p ranges from 0 to 0.95, said polymer being present in an amount of 0.01-10 percent by weight thereof and an effective amount of at least one adjuvant employed in cosmetic compositions for the skin, said adjuvant being selected so as to provide one of a cream or lotion for the hands or face, an anti-solar composition, a make-up remover milk, a foamable liquid for the bath or a deodorant composition.

9. A hair treating lotion composition comprising an aqueous or hydroalcoholic solution of at least one polymer having recurring units of the formula

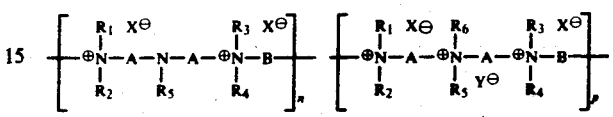

wherein
A is polymethylene having 2-10 carbon atoms;
B is selected from polymethylene having 3-10 carbon atoms, xylylidenyl —CH$_2$—C$_6$H$_4$—CH$_2$— ortho, meta or para, —(CH$_2$)$_x$—O—(CH$_2$)$_x$— wherein x is 2 or 3, or —CH$_2$—CHOH—CH$_2$—;
R$_1$ and R$_3$ each independently represent alkyl having 1-12 carbon atoms;
R$_2$ and R$_4$ each independently represent alkyl having 1-20 carbon atoms;
R$_5$ is hydrogen or alkyl, aryl or arylalkyl containing a maximum of 20 carbon atoms or cycloalkyl having 5 or 6 carbon atoms;
R$_6$ is alkyl or arylalkyl containing a maximum of 20 carbon atoms;
X$^\ominus$ is a halide anion;
Y$^\ominus$ is selected from a halide anion, SO$_4$H$^\ominus$ or CH$_3$SO$_4{}^\ominus$; and
n and p are whole numbers with p being able to be 0, such that the ratio p/n+p ranges from 0 to 0.95, said polymer being present in an amount of 0.01 to 10 percent by weight of said composition and said composition having a pH from 6 to 8.

10. A shampoo composition comprising at least one polymer having recurring units of the formula

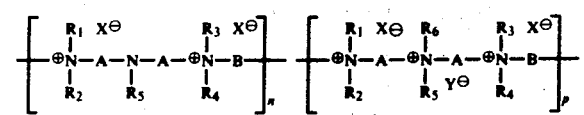

wherein
A is polymethylene having 2-10 carbon atoms;
B is selected from polymethylene having 3-10 carbon atoms, xylylidenyl —CH$_2$—C$_6$H$_4$—CH$_2$— ortho, meta or para, —(CH$_2$)$_x$—O—(CH$_2$)$_x$— wherein x is 2 or 3, or —CH$_2$—CHOH—CH$_2$—;
R$_1$ and R$_3$ each independently represent alkyl having 1-12 carbon atoms;
R$_2$ and R$_4$ each independently represent alkyl having 1-20 carbon atoms;
R$_5$ is hydrogen or alkyl, aryl or arylalkyl containing a maximum of 20 carbon atoms or cycloalkyl having 5 or 6 carbon atoms;
R$_6$ is alkyl or arylalkyl containing a maximum of 20 carbon atoms;
X$^\ominus$ is a halide anion;
Y$^\ominus$ is selected from a halide anion, SO$_4$H$^\ominus$ or CH$_3$SO$_4{}^\ominus$; and n and p are whole numbers with p being able to be 0, such that the ratio p/n+p ranges from 0 to 0.95, said polymer being present in an amount of 0.01 to 3 percent by weigh thereof and an effective amount of a cationic, non-ionic or anionic detergent.

11. The shampoo composition of claim 10 wherein said detergent is present in an amount between 5 and 30 weight percent of said composition.

12. A hair setting lotion comprising an aqueous, alcoholic or hydroalcoholic solution of at least one polymer having recurring units of the formula

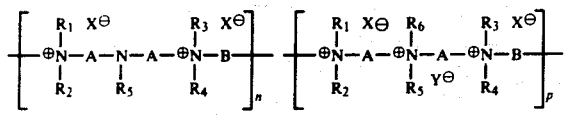

wherein
A is polymethylene having 2–10 carbon atoms;
B is selected from polymethylene having 3–10 carbon atoms, xylylidenyl $-CH_2-C_6H_4-CH_2-$ ortho, meta or para, $-(CH_2)_x-O-(CH_2)_x-$ wherein x is 2 or 3, or $-CH_2-CHOH-CH_2-$;
$R_1$ and $R_3$ each independently represent alkyl having 1–12 carbon atoms;
$R_2$ and $R_4$ each independently represent alkyl having 1–20 carbon atoms;
$R_5$ is hydrogen or alkyl, aryl or arylalkyl containing a maximum of 20 carbon atoms or cycloalkyl having 5 or 6 carbon atoms;
$R_6$ is alkyl or arylalkyl containing a maximum of 20 carbon atoms;
$X^\ominus$ is a halide anion;
$Y^\ominus$ is selected from a halide anion, $SO_4H^\ominus$ or $CH_3SO_4^\ominus$; and
n and p are whole numbers with p being able to be 0, such that the ratio p/n+p ranges from 0 to 0.95, said polymer being present in an amount between 0.1 and 5 percent by weight of said composition, and said composition having a pH ranging between 3 and 9.

13. The hair setting lotion of claim 13 which also includes another cosmetic resin selected from polyvinylpyrrolidone, a copolymer of polyvinylpyrrolidone and vinyl acetate or a copolymer of crotonic acid and vinyl acetate, said another cosmetic resin being present in an amount between 0.1 and 5 percent by weight of said composition.

14. A hair dye composition comprising a carrier, at least one polymer having recurring units of the formula wherein
A is polymethylene having 2–10 carbon atoms;
B is selected from polymethylene having 3–10 carbon atoms, xylylidenyl $-CH_2-C_6H_4-CH_2-$ ortho, meta or para, $-(CH_2)_x-O-(CH_2)_x-$ wherein x is 2 or 3, or $-CH_2-CHOH-CH_2-$;
$R_1$ and $R_3$ each independently represent alkyl having 1–12 carbon atoms;
$R_2$ and $R_4$ each independently represent alkyl having 1–20 carbon atoms;
$R_5$ is hydrogen or alkyl, aryl or arylalkyl containing a maximum of 20 carbon atoms or cycloalkyl having 5 or 6 carbon atoms;
$R_6$ is alkyl or arylalkyl containing a maximum of 20 carbon atoms;
$X^\ominus$ is a halide anion;
$Y^\ominus$ is selected from a halide anion, $SO_4H^\ominus$ or $CH_3SO_4^\ominus$; and
n and p are whole numbers with p being able to be 0, such that the ratio p/n+p ranges from 0 to 0.95, said polymer being present in an amount between 0.1 and 10 percent by weight of said composition and an effective amount of a hair dye.

15. A hair lacquer composition comprising an alcoholic or hydroalcoholic solution of a hair lacquer cosmetic resin and at least one polymer having recurring units of the formula wherein
A is polymethylene having 2–10 carbon atoms;
B is selected from polymethylene having 3–10 carbon atoms, xylylidenyl $-CH_2-C_6H_4-CH_2-$ ortho, meta or para, $-(CH_2)_x-O-(CH_2)_x-$ wherein x is 2 or 3, or $-CH_2-CHOH-CH_2-$;
$R_1$ and $R_3$ each independently represent alkyl having 1–12 carbon atoms;
$R_2$ and $R_4$ each independently represent alkyl having 1–20 carbon atoms;
$R_5$ is hydrogen or alkyl, aryl or arylalkyl containing a maximum of 20 carbon atoms or cycloalkyl having 5 or 6 carbon atoms;
$R_6$ is alkyl or arylalkyl containing a maximum of 20 carbon atoms;
$X^\ominus$ is a halide anion;
$Y^\ominus$ is selected from a halide anion, $SO_4H^\ominus$ or $CH_3SO_4^\ominus$; and
n and p are whole numbers with p being able to be 0, such that the ratio p/n+p ranges from 0 to 0.95, said solution being packaged under pressure together with an aerosol propellant in an aerosol container, said hair lacquer cosmetic resin being present in an amount between 0.5 and 3 percent by weight of said composition and said polymer being present in an amount between 0.1 and 3 percent by weight of said composition.

16. A hair restructuring lotion comprising at least one hair restructuring agent present in an amount between 0.1 and 10 percent by weight thereof and at least one polymer having recurring units of the formula wherein
A is polymethylene having 2–10 carbon atoms;
B is selected from polymethylene having 3–10 carbon atoms, xylylidenyl $-CH_2-C_6H_4-CH_2-$ ortho, meta or para, $-(CH_2)_x-O-(CH_2)_x-$ wherein x is 2 or 3, or $-CH_2-CHOH-CH_2-$;

$R_1$ and $R_3$ each independently represent alkyl having 1-12 carbon atoms;

$R_2$ and $R_4$ each independently represent alkyl having 1-20 carbon atoms;

$R_5$ is hydrogen or alkyl, aryl or arylalkyl containing a maximum of 20 carbon atoms or cycloalkyl having 5 or 6 carbon atoms;

$R_6$ is alkyl or arylalkyl containing a maximum of 20 carbon atoms;

$X^\ominus$ is a halide anion;

$Y^\ominus$ is selected from a halide anion, $SO_4H^\ominus$ or $CH_3SO_4^\ominus$; and n and p are whole numbers with p being able to be 0, such that the ratio $p/n+p$ ranges from 0 to 0.95, present in an amount between 0.1 and 5 percent by weight of said composition.

17. A hair pretreatment composition for application to the hair prior to an anionic or non-ionic shampoo, or prior to an oxidation dyeing operation followed by an anionic or non-ionic shampoo, or prior to a permanent waving treatment comprising an aqueous or hydroalcoholic solution of the polymer having recurring units of the formula

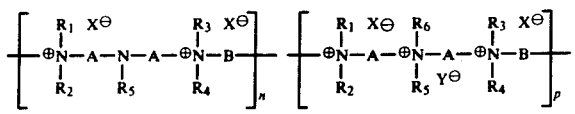

wherein

A is polymethylene having 2-10 carbon atoms;

B is selected from polymethylene having 3-10 carbon atoms, xylylidenyl —$CH_2$—$C_6H_4$—$CH_2$— ortho, meta or para, —$(CH_2)_x$—O—$(CH_2)_x$— wherein x is 2 or 3, or —$CH_2$—CHOH—$CH_2$—;

$R_1$ and $R_3$ each independently represent alkyl having 1-12 carbon atoms;

$R_2$ and $R_4$ each independently represent alkyl having 1-20 carbon atoms;

$R_5$ is hydrogen or alkyl, aryl or arylalkyl containing a maximum of 20 carbon atoms or cycloalkyl having 5 or 6 carbon atoms;

$R_6$ is alkyl or arylalkyl containing a maximum of 20 carbon atoms;

$X^\ominus$ is a halide anion;

$Y^\ominus$ is selected from a halide anion, $SO_4H^\ominus$ or $CH_3SO_4^\ominus$; and n and p are whole numbers with p being able to be 0, such that the ratio $p/n+p$ ranges from 0 to 0.95, said polymer being present in an amount between 0.1 and 10 percent by weight of said composition and said composition having a pH between 3 and 9.

18. A process for preparing a polymer having recurring units of the formula

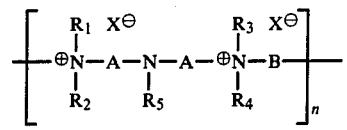

wherein

A is polymethylene having 2-10 carbon atoms;

B is selected from polymethylene having 3-10 carbon atoms, xylylidenyl —$CH_2$—$C_6H_4$—$CH_2$— ortho, meta or para, —$(CH_2)_x$—O—$(CH_2)_x$— wherein x is 2 or 3, or —$CH_2$—CHOH—$CH_2$—;

$R_1$ and $R_3$ each independently represent alkyl having 1-12 carbon atoms;

$R_2$ and $R_4$ each independently represent alkyl having 1-20 carbon atoms;

$R_5$ is hydrogen or alkyl, aryl or arylalkyl containing a maximum of 20 carbon atoms or cycloalkyl having 5 or 6 carbon atoms;

$X^\ominus$ is a halide anion;

n is a whole number, comprising polycondensing a triamine of the formula $R_1R_2N$-A-N($R_5$)-A-$NR_3R_4$ with an essentially equimolar amount of a dihalide of the formula X-B-X, wherein $R_1$, $R_2$, $R_3$, $R_4$, $R_5$, A, B and X have the meanings set forth above, and wherein said process is undertaken at a temperature between 10° and 150° C.

19. A process of preparing a polymer having recurring units of the formula

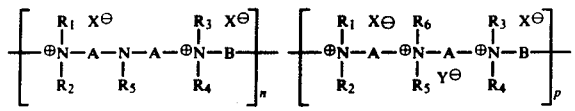

wherein

A is polymethylene having 2-10 carbon atoms;

B is selected from polymethylene having 3-10 carbon atoms, xylylidenyl —$CH_2$—$C_6H_4$—$CH_2$— ortho, meta or para, —$(CH_2)_x$—O—$(CH_2)_x$— wherein x is 2 or 3, or —$CH_2$—CHOH—$CH_2$—;

$R_1$ and $R_3$ each independently represent alkyl having 1-12 carbon atoms;

$R_2$ and $R_4$ each independently represent alkyl having 1-20 carbon atoms;

$R_5$ is hydrogen or alkyl, aryl or arylalkyl containing a maximum of 20 carbon atoms or cycloalkyl having 5 or 6 carbon atoms;

$R_6$ is alkyl or arylalkyl containing a maximum of 20 carbon atoms;

$X^\ominus$ is a halide anion;

$Y^\ominus$ is selected from a halide anion, $SO_4H^\ominus$ or $CH_3SO_4^\ominus$; and n and p are whole numbers such that the ratio $p/n+p$ ranges up to 0.95, comprising polycondensing a triamine of the formula $R_1R_2N$-A-N($R_5$)-A-$NR_3R_4$ with an essentially equimolar amount of a dihalide of the formula X-B-X to form an intermediate polymer and reacting said intermediate polymer with a maximum of 3 moles of a compound of the formula $R_6$-Y, wherein $R_1$, $R_2$, $R_3$, $R_4$, $R_5$, $R_6$, A, B, X and Y have the meanings set forth above, and wherein said process is carried out at a temperature between 10° and 150° C.

* * * * *